(12) United States Patent
Peltola

(10) Patent No.: US 12,251,575 B2
(45) Date of Patent: Mar. 18, 2025

(54) PLAN ANALYSIS AND GUIDANCE USING VOICE COMMANDS AND HUMAN LANGUAGE PROCESSING

(71) Applicant: SIEMENS HEALTHINEERS INTERNATIONAL AG, Steinhausen (CH)

(72) Inventor: Jarkko Peltola, Tuusula (FI)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 241 days.

(21) Appl. No.: 17/842,317

(22) Filed: Jun. 16, 2022

(65) Prior Publication Data

US 2023/0405356 A1    Dec. 21, 2023

(51) Int. Cl.
*A61N 5/10*    (2006.01)

(52) U.S. Cl.
CPC ......... *A61N 5/1031* (2013.01); *A61N 5/1038* (2013.01); *A61N 2005/1041* (2013.01)

(58) Field of Classification Search
None
See application file for complete search history.

(56) References Cited

U.S. PATENT DOCUMENTS

| | | | | |
|---|---|---|---|---|
| 6,526,415 B2* | 2/2003 | Smith | ...................... | G06F 16/40 704/7 |
| 6,850,252 B1* | 2/2005 | Hoffberg | .............. | H04N 21/475 380/252 |
| 7,813,822 B1* | 10/2010 | Hoffberg | ................ | H04N 7/163 381/73.1 |
| 8,009,803 B2* | 8/2011 | Nord | ...................... | A61N 5/103 378/65 |
| 8,156,206 B2* | 4/2012 | Kiley | ...................... | H04W 4/02 709/228 |
| 8,238,520 B2* | 8/2012 | Nord | ...................... | A61N 5/103 378/65 |
| 9,507,886 B2* | 11/2016 | Fiege | ...................... | G06N 3/126 |
| 9,987,504 B2* | 6/2018 | Nord | ...................... | A61N 5/103 |
| 9,990,731 B2* | 6/2018 | Scheib | .................... | G06F 18/24 |
| 10,112,059 B2* | 10/2018 | Toimela | ............... | A61N 5/1031 |

(Continued)

FOREIGN PATENT DOCUMENTS

WO    WO-2022/051068 A1    3/2022

OTHER PUBLICATIONS

International Search Report and Written Opinion on PCT App. PCT/EP2023/065372 dated Aug. 30, 2023 (12 pages).

*Primary Examiner* — Marcus H Taningco
*Assistant Examiner* — Djura Malevic
(74) *Attorney, Agent, or Firm* — Foley & Lardner LLP

(57) ABSTRACT

Embodiments described herein provide for radiotherapy treatment plan analysis and guidance using voice commands and human language processing. A processor monitors a computer model generating a radiation therapy treatment plan comprising a projected dose-volume distribution for a structure of a patient or an attribute of the radiation therapy treatment plan. The processor receives a query indicating the structure of the patient. The processor generates a query term based on the received query. The processor retrieves data associated with the query term by querying data generated based on monitoring the computer model. The processor transmits the retrieved data to computer device.

20 Claims, 7 Drawing Sheets

(56) References Cited

U.S. PATENT DOCUMENTS

| | | | |
|---|---|---|---|
| 10,152,951 B2* | 12/2018 | Waschbuesch | G06F 3/04847 |
| 10,402,972 B2* | 9/2019 | Kuusela | G06T 7/0012 |
| 10,456,600 B2* | 10/2019 | Owens | A61N 5/1045 |
| 10,675,486 B2* | 6/2020 | Toimela | A61N 5/103 |
| 10,881,877 B2* | 1/2021 | Scheib | G06T 7/0012 |
| 11,191,979 B2* | 12/2021 | Nord | A61N 5/103 |
| 11,266,858 B2* | 3/2022 | Toimela | A61N 5/1071 |
| 11,358,004 B2* | 6/2022 | Wu | G16H 50/50 |
| 11,495,355 B2* | 11/2022 | McNutt | G16H 50/70 |
| 11,615,873 B2* | 3/2023 | Nguyen | G16H 30/40 600/300 |
| 11,969,280 B2* | 4/2024 | Min | G06F 18/10 |
| 2007/0203902 A1* | 8/2007 | Bauerle | G06F 16/283 707/999.005 |
| 2010/0183121 A1* | 7/2010 | Riker | G16H 70/20 378/65 |
| 2010/0228116 A1* | 9/2010 | Lu | A61N 5/103 703/11 |
| 2011/0268249 A1* | 11/2011 | Nord | A61N 5/103 378/65 |
| 2012/0136677 A1* | 5/2012 | Ziegenhein | G16H 20/40 705/2 |
| 2013/0197878 A1* | 8/2013 | Fiege | G06F 30/20 703/2 |
| 2013/0304503 A1* | 11/2013 | Kuefer | A61N 5/1031 705/2 |
| 2014/0275706 A1* | 9/2014 | Dean | A61N 5/1031 600/1 |
| 2014/0337510 A1* | 11/2014 | Gesmann | G06F 11/3466 709/224 |
| 2016/0287906 A1* | 10/2016 | Nord | A61N 5/103 |
| 2017/0076046 A1* | 3/2017 | Barnes | G06F 16/951 |
| 2017/0083682 A1* | 3/2017 | McNutt | A61N 5/1031 |
| 2017/0200276 A1* | 7/2017 | Scheib | A61N 5/1071 |
| 2018/0018864 A1* | 1/2018 | Baker | G08B 21/182 |
| 2018/0117358 A1* | 5/2018 | Nord | A61N 5/1036 |
| 2018/0236264 A1* | 8/2018 | Scheib | A61N 5/1075 |
| 2018/0250530 A1* | 9/2018 | Nord | A61N 5/103 |
| 2019/0043187 A1* | 2/2019 | Kuusela | A61B 6/032 |
| 2019/0054320 A1* | 2/2019 | Owens | A61B 6/032 |
| 2019/0083814 A1* | 3/2019 | Tallinen | A61N 5/1045 |
| 2020/0075148 A1* | 3/2020 | Nguyen | G16H 30/40 |
| 2020/0197729 A1* | 6/2020 | Owens | A61N 5/1045 |
| 2020/0282232 A1* | 9/2020 | Khuntia | A61N 5/1031 |
| 2020/0282234 A1* | 9/2020 | Folkerts | G06T 7/0012 |
| 2020/0286601 A1* | 9/2020 | Khuntia | G16H 15/00 |
| 2020/0312449 A1* | 10/2020 | Keranen | G16H 20/40 |
| 2020/0353286 A1* | 11/2020 | Wu | A61N 5/1031 |
| 2020/0384289 A1* | 12/2020 | Smith | A61N 5/1031 |
| 2021/0090694 A1* | 3/2021 | Colley | G16H 15/00 |
| 2021/0110897 A1* | 4/2021 | Ginsburg | G16H 10/60 |
| 2022/0001209 A1* | 1/2022 | Owens | A61N 5/1071 |
| 2022/0054863 A1* | 2/2022 | Nord | A61N 5/103 |
| 2022/0126116 A1* | 4/2022 | Harrer | A61N 5/1031 |
| 2023/0293907 A1* | 9/2023 | Shade | A61N 5/1031 600/1 |
| 2023/0405356 A1* | 12/2023 | Peltola | A61N 5/103 |

* cited by examiner

Monitoring a computer model generating a radiation therapy treatment plan comprising a projected dose-volume distribution for a structure of a patient, the computer model receiving at least an image of the structure of the patient and a dose objective, wherein the computer model iteratively calculates the treatment plan by projecting different doses for the structure of the patient until the computer model converges onto the projected dose-volume distribution. 702

In response to a presentation of the radiation therapy treatment plan by a computer device, receiving a query indicating the structure of the patient and a new attribute of the radiation therapy treatment plan. 704

Instructing the computer model to execute a simulation of an additional iteration using the new attribute. 706

FIG. 7

PLAN ANALYSIS AND GUIDANCE USING VOICE COMMANDS AND HUMAN LANGUAGE PROCESSING

TECHNICAL FIELD

This application relates generally to radiotherapy treatment plan analysis and guidance using voice commands and human language processing.

BACKGROUND

Radiotherapy (radiation-based therapy) is used as a cancer treatment to emit high doses of radiation that can kill cells or shrink tumors. The target region of a patient's body that is intended to receive radiation (e.g., a tumor) is referred to as the planning target volume (PTV). The goal of radiotherapy is to deliver enough radiation to the PTV to kill the cancerous cells during the radiotherapy treatment. However, organs or anatomical regions that are adjacent to, or surrounding, the PTV can be in the way of radiation beams and can receive enough radiation to damage or harm such organs or anatomical regions. These organs or anatomical regions are referred to as organs at risk (OARs).

It can be important to accurately estimate the amount of radiation the OARs will receive during treatment to avoid "overdosing" the OARs with radiation. Oftentimes, physicians attempt to avoid such overdosing by calculating a percentage (e.g., 10%) of the total radiation that is directed at the PTV and guessing if the calculated amount would have too much of a negative impact on the OARs. Other physicians may use a computer to execute an algorithm given objectives of a radiotherapy treatment plan to estimate the amount of radiation that will impact the OARs. Each of these methods may fail to accurately predict whether a certain radiotherapy treatment plan will cause severe damage to the OARs given the many real-world variables that may have an impact. Further, even if a physician could successfully predict the amount of radiation an OAR would receive under a radiotherapy treatment plan, if the physician determines the radiotherapy treatment plan would not work, the physician may not be able to figure out how to adjust the plan to avoid harming the OARs while still providing the necessary treatment to the PTV.

SUMMARY

For the aforementioned reasons, there is a desire for a system that can automatically determine an optimized radiotherapy treatment plan based on physician configured objectives. One attempt to determine an optimized radiotherapy treatment plan is to minimize a total cost function that is constructed as a sum of cost terms per the objectives that a physician seeks to be met. Another attempt to determine an optimized radiotherapy treatment plan is to use machine learning models that have been trained to predict the amount of radiation that different OARs receive during treatment of a PTV. A computer that executes a model comprising a cost function or machine learning model may receive inputs from a physician indicating objectives (e.g., limits to the amounts of radiation a physician is comfortable with different OARs receiving during treatment), a dose objective for treating the PTV, and/or a contoured image that indicates the area(s) of a patient to which the radiotherapy treatment plan is directed and/or the structures surrounding the area. The model may output a predicted amount of radiation the OARs may receive under the radiotherapy treatment plan. The computer may compare the expected radiation dosage the OARs are projected to receive under the plan to the radiation limits. If the expected radiation dosage for an OAR exceeds an input limit, the computer may adjust the radiotherapy treatment plan and execute the model with the adjusted plan. The computer may iteratively perform this process until determining a better plan could not be identified given the input objectives by the physician.

Upon identifying the optimal radiotherapy treatment plan, the physician may review the expected results under the plan (e.g., the amount of radiotherapy the OARs will receive). If the physician determines the results of the plan are unacceptable (e.g., an OAR is receiving too much radiation), the physician may input a new set of objectives. Because the computer model that generates the optimal radiotherapy treatment plan is often computationally complex and the physician may not be computer savvy, the process of identifying the plan may be a "black box" to the physician. Accordingly, the physician may not have gained any insights from the originally generated plan and the physician may input the new set of objectives without knowing the cause of the unacceptable results. The computer may receive the new objectives and repeat the iterative process using the model as described above to determine a new optimal plan for treatment. This process can often take a large amount of time and can require a large amount of computer resources as the computer repeatedly executes the model to determine a new optimized plan. The problem may only get worse as the physician repeatedly inputs new objectives until finding a plan with which the physician is satisfied.

To overcome the aforementioned technical deficiencies, a computer implementing the systems and methods described herein may maintain a query space (e.g., a buffer, cache, database, or other location in memory). For instance, the computer may store a model and perform the process described above by iteratively executing the model to determine an optimal radiotherapy treatment plan (e.g., a set of radiotherapy plan attributes, such as a radiotherapy machine gantry position or angle) given an input set of objectives, a contoured image, and/or a dose objective for a PTV. For each iteration, the computer may receive the output radiation amount the machine learning model predicts the different OARs will receive. The computer may store the output radiation amounts in the query space in memory. Accordingly, if a physician treating a patient using the radiotherapy treatment plan submits a query (e.g., orally asks a question) about how the optimal plan was determined, the system may respond to the query by retrieving data from the query space in memory. The physician may view and use the retrieved data to better target objective adjustments to make to improve the unacceptable results of an optimized radiotherapy treatment plan.

Furthermore, a computer implementing the systems and methods described herein may enable a physician to adjust the objectives of a radiotherapy treatment plan in real-time after obtaining a projected optimal radiotherapy treatment plan without repeating the iterative execution of the machine learning model. To do so, the computer may calculate the amount of radiation different OARs may receive given an input set of objectives, a contoured image, and/or a dose objective for a PTV. The computer may then present the amounts of radiation on a computing device being accessed by a physician. The physician may provide an input adjusting one or more of the input objectives to the computing device. In some cases, a physician may add new input objectives for the plan. Adding the new inputs may help avoid any clashes with existing methods for fine-tuning the optimal plan. The computing device may forward the objective adjustments to the computer. Upon receiving the objective adjustments, the computer may execute the model beginning with the radiotherapy treatment plan attributes of the previously optimized plan and adjust the plan attributes according to the adjusted objectives. The computer may do so for a single iteration or repeatedly until the results converge to a new optimal radiotherapy treatment plan. The computer may then present the results on the physician's computing device to illustrate the impact of the adjusted objective. In this way, by initializing the plan attributes to the radiotherapy treatment plan attributes of the previously optimized plan to converge to a new plan, the computer implementing the systems and methods described herein may generate a new optimized plan with less latency and while using less computing resources than in other systems that repeat the entire process upon receiving a similar physician input.

In one aspect, a method may comprise monitoring, by a processor, a computer model generating a radiation therapy treatment plan comprising a projected dose-volume distribution for a structure of a patient, the computer model receiving at least an image of the structure of the patient and a dose objective, wherein the computer model iteratively calculates the treatment plan by projecting different doses for the structure of the patient until the computer model converges onto the projected dose-volume distribution; receiving, by the processor from a computer device presenting the radiation treatment plan, a query indicating the structure of the patient or an attribute of the radiation therapy treatment plan; generating, by the processor, a query term based on the received query; retrieving, by the processor, data associated with the query term by querying data generated based on monitoring the computer model; and transmitting, by the processor, the retrieved data to computer device, wherein the retrieved data corresponds to a second structure and at least one projected different dose.

In some implementations, the method further comprises instructing, by the processor, the computer device to display the retrieved data in a window associated with the presentation of the radiation therapy treatment plan. In some implementations, the display is at least one of a chart, a sentence in a natural language, or a number. In some implementations, the processor executes a natural language processing protocol to identify the query term.

In some implementations, retrieving the data associated with the query term comprises retrieving a positive or negative correlation between the first structure and the second structure. In some implementations, the radiation therapy treatment plan further comprises a monitored unit (MU) parameter, wherein the computer model converges onto the projected dose-volume distribution and the MU parameter. In some implementations, the computer model converges onto the projected dose-volume distribution and the MU parameter using a cost function, and wherein the processor monitors a parameter of the cost function associated with at least a portion of a projected dose-volume distribution from at least one iteration and a corresponding MU. In some implementations, the second structure is the same as the structure.

In another aspect, a system may comprise a processor configured to monitor a computer model generating a radiation therapy treatment plan comprising a projected dose-volume distribution for a structure of a patient, the computer model receiving at least an image of the structure of the patient and a dose objective, wherein the computer model iteratively calculates the treatment plan by projecting different doses for the structure of the patient until the computer model converges onto the projected dose-volume distribution; receive, from a computer device presenting the radiation treatment plan, a query indicating the structure of the patient or an attribute of the radiation therapy treatment plan; generate a query term based on the received query; retrieve data associated with the query term by querying data generated based on monitoring the computer model; and transmit the retrieved data to computer device, wherein the retrieved data corresponds to a second structure and at least one projected different dose.

In some implementations, the processor is further configured to instruct the computer device to display the retrieved data in a window associated with the presentation of the radiation therapy treatment plan. In some implementations, the display is at least one of a chart, a sentence in a natural language, or a number. In some implementations, the processor is configured to generate the query term by executing a natural language processing protocol to identify the query term. In some implementations, the processor is configured to retrieve the data associated with the query term by retrieving a positive or negative correlation between the first structure and the second structure.

In some implementations, the radiation therapy treatment plan further comprises a monitored unit (MU) parameter, wherein the computer model converges onto the projected dose-volume distribution and the MU parameter. In some implementations, the computer model converges onto the projected dose-volume distribution and the MU parameter using a cost function, and wherein the processor is configured to monitor parameters of the cost function associated with at least a portion of a projected dose-volume distribution from at least one iteration and a corresponding MU. In some implementations, the second structure is the same as the structure.

In another aspect, a method may comprise monitoring, by a processor, a computer model generating a radiation therapy treatment plan comprising a projected dose-volume distribution for a structure of a patient, the computer model receiving at least an image of the structure of the patient and a dose objective, wherein the computer model iteratively calculates the treatment plan by projecting different doses for the structure of the patient until the computer model converges onto the projected dose-volume distribution; in response to a presentation of the radiation therapy treatment plan by a computer device, receiving, by the processor, a query indicating the structure of the patient or an attribute of the radiation therapy treatment plan and a new objective of the radiation therapy treatment plan; and instructing, by the processor, the computer model to execute a simulation of an additional iteration using the new objective.

In some implementations, the method further comprises instructing, by the processor, the computer device to display data associated with a new radiation therapy treatment plan using the new objective. In some implementations, the new radiation therapy treatment plan includes a cost function parameter associated with the new objective. In some implementations, at least a difference between the radiation treatment plan and the new radiation treatment plan is indicated.

BRIEF DESCRIPTION OF THE DRAWINGS

Non-limiting embodiments of the present disclosure are described by way of example with reference to the accompanying figures, which are schematic and are not intended to be drawn to scale. Unless indicated as representing the background art, the figures represent aspects of the disclosure.

FIG. 7 illustrates another flow diagram of a process executed in a radiotherapy treatment plan system, according to an embodiment.

DETAILED DESCRIPTION

Figure 1:
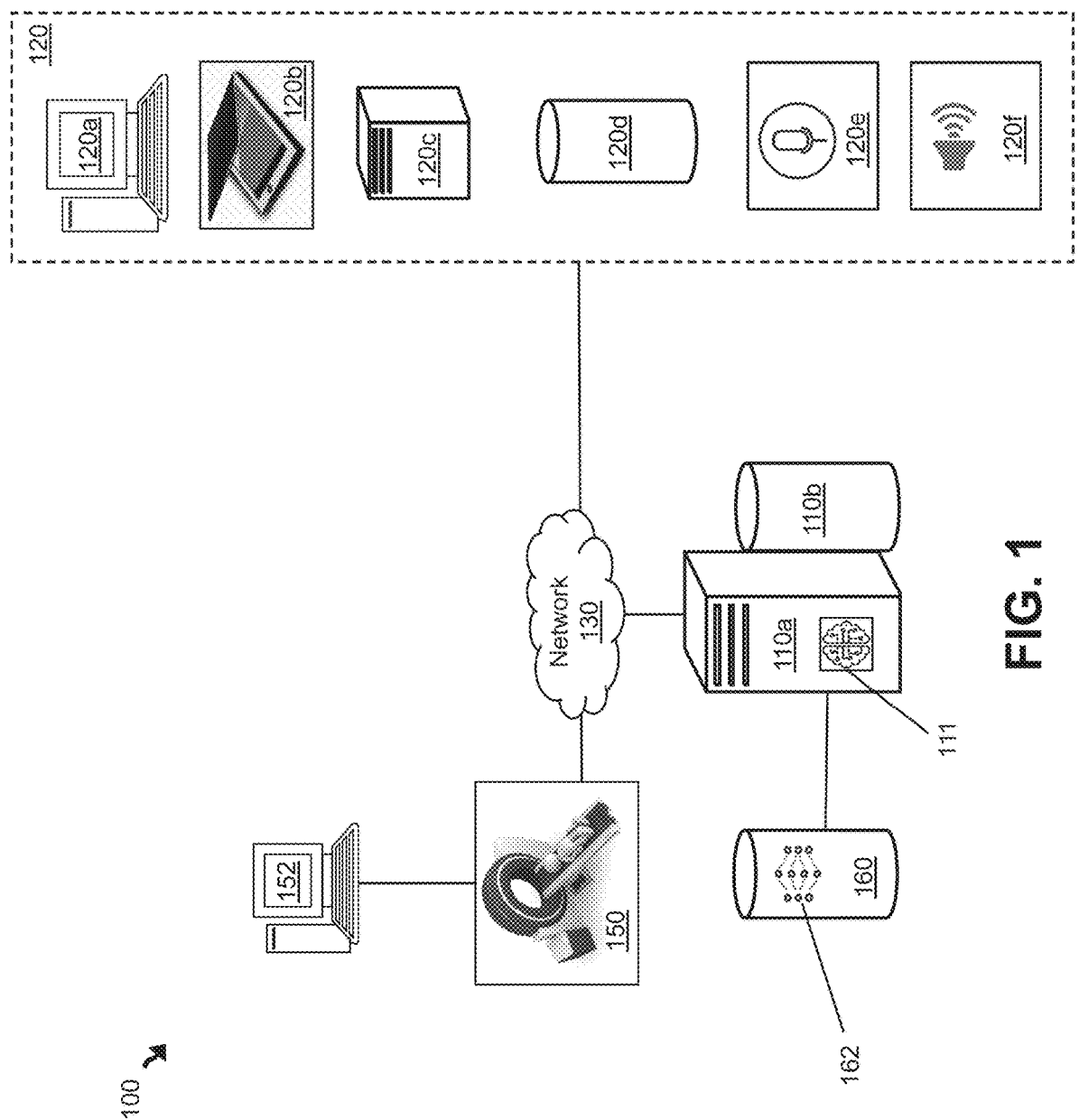
FIG. 1 illustrates components of a radiotherapy treatment plan system, according to an embodiment.

Reference will now be made to the illustrative embodiments depicted in the drawings, and specific language will be used here to describe the same. It will nevertheless be understood that no limitation of the scope of the claims or this disclosure is thereby intended. Alterations and further modifications of the inventive features illustrated herein, and additional applications of the principles of the subject matter illustrated herein, which would occur to one skilled in the relevant art and having possession of this disclosure, are to be considered within the scope of the subject matter disclosed herein. Other embodiments may be used and/or other changes may be made without departing from the spirit or scope of the present disclosure. The illustrative embodiments described in the detailed description are not meant to be limiting of the subject matter presented.

The radiotherapy planning process is often complicated and involves a physician operating a computer executing a computer model to determine an optimized radiotherapy treatment plan to cure a PTV in a patient. Most of the communication between the physician and the computer involves complex and unclear terminology, which is often wrapped in mathematical concepts. For example, in a typical situation, the optimization process produces a plan candidate which is a trade-off/compromise between multiple dimensions. It can be difficult to know what caused the computer to generate the plan and what needs to be done to achieve a different result (e.g., generate a different plan based on adjusted objectives). Some solutions to this problem involve an optimization dialogue in which the computer that generates the plan provides the physician with individual cost function terms that correspond to the different objectives of the plan. However, in such solutions, it is still up to the physician to determine how to adjust the plan to obtain more desirable results (e.g., results in which certain organs of a patient receive less radiation during treatment).

To overcome the aforementioned technical problems, a computer implementing the systems and methods described herein may enable a physician to query for analytics from the computer regarding the plan optimization process and how the plan was developed (e.g., ask for data generated from individual iterations of executing the computer model in generating the plan). The physician can ask specific questions about the status of certain features, such as questions about achieved objectives and/or clinical goals. The physician can also ask for guidance as to how to adjust any of the objectives to obtain a more desirable plan. This process can be facilitated by a graphical user interface provided by the computer and/or through the use of voice commands using artificial intelligence packages that can translate spoken language to a textual format and vice versa. The systems and methods provide an improvement over previous systems, which are often limited to showing a dialogue box showing relative cost function values for the different objectives, and/or indications of whether individual objectives are in conflict with each other.

As will be described below, a server (referred to herein as an analytics server) implementing the systems and methods described herein can execute a plan optimizer model comprising instructions for an optimization algorithm or a machine learning model (e.g., a neural network or another machine learning model) to determine an optimal and adjustable radiotherapy treatment plan and provide an analysis regarding how the plan was generated. In a non-limiting example, the server may execute a plan optimizer model using an image (e.g., a two or three dimensional image) of a patient contoured with the individual structures (e.g., organs) depicted in the image, a dose objective indicating an amount of radiation a physician seeks to provide a PTV, and/or radiotherapy plan attributes as input. Upon doing so, the plan optimizer model may output an expected amount of radiation the OARs will receive according to the radiotherapy plan attributes and the dose objective. The server may store the output in memory and compare the output to objectives indicating limits to the amount of radiation the physician is comfortable with the OARs surrounding or adjacent to the PTV that is being treated receiving. The server may iteratively perform this process, storing each output from each execution of the plan optimizer model, until the server identifies a "converged" radiotherapy treatment plan that most accurately or most closely satisfies the objectives. A physician may view the converged radiotherapy treatment plan and query the server as to why the radiotherapy treatment plan falls out of the input objectives for any point of the treatment. The server may receive the query and retrieve data from the output stored in memory to use in responding to the request. The physician may view the retrieved data to determine whether to implement the optimal plan or to adjust the attributes in an attempt to obtain a more optimal plan (e.g., a plan in which the OARs receive radiation at a more acceptable level to the physician).

If the physician determines the results are not satisfactory, the physician may adjust the objectives for the plan (e.g., increase or decrease the acceptable dosage limit for an OAR during treatment). After the server receives an indication of the adjustment, the server may execute the plan optimizer model according to the adjusted objectives by adjusting the radiotherapy treatment plan attributes of the previously optimized plan according to the adjusted objectives. The server may adjust the attributes until the model outputs a new converged radiotherapy treatment plan. In this way, the server may provide physicians with real-time analysis of a radiotherapy treatment plan and provide the physicians with the ability to adjust the plan on the fly without requiring the computer resources and time that would be necessary for iterative execution of the plan optimizer model for each adjustment. FIG. 1 is a non-limiting example of components of a system in which such a server operates.

FIG. 1 illustrates components of a radiotherapy treatment plan system 100, according to an embodiment. The system 100 may include an analytics server 110a, system database 110*b*, electronic data sources 120*a-f* (collectively electronic data sources 120), a medical device 150 coupled to a medical computing device 152, and an external database 160. Various components depicted in FIG. 1 may belong (e.g., be physically located at) to a radiotherapy clinic at which patients receive radiotherapy treatment, in some cases via one or more radiotherapy machines located within the clinic (e.g., medical device 150). The above-mentioned components may be connected to each other through a network 130. Examples of the network 130 may include, but are not limited to, private or public LAN, WLAN, MAN, WAN, and the Internet. The network 130 may include wired and/or wireless communications according to one or more standards and/or via one or more transport mediums.

The communication over the network 130 may be performed in accordance with various communication protocols such as Transmission Control Protocol and Internet Protocol (TCP/IP), User Datagram Protocol (UDP), and IEEE communication protocols. In one example, the network 130 may include wireless communications according to Bluetooth specification sets or another standard or proprietary wireless communication protocol. In another example, the network 130 may also include communications over a cellular network, including, e.g., a GSM (Global System for Mobile Communications), CDMA (Code Division Multiple Access), EDGE (Enhanced Data for Global Evolution) network.

The system 100 is not confined to the components described herein and may include additional or other components, not shown for brevity, which are to be considered within the scope of the embodiments described herein.

The analytics server 110*a* may store one or more plan optimizer models 111. The plan optimizer models 111 may be or include a machine learning model such as a neural network, a random forest, a clustering machine learning model, a support vector machine, a regression model, etc., and/or an optimization algorithm. The plan optimizer models 111 may be configured to receive images such as CT scans of patients, radiotherapy treatment plan attributes, and/or dose objectives of a PTV. Based on this input, the plan optimizer models 111 may output the expected radiation dosage that structures surrounding a PTV will receive as a result of the radiation that will be applied to the PTV.

As described herein, treatment attributes may be or include any attributes related to treating patients at a radiotherapy clinic and/or using a radiotherapy machine. Treatment attributes may include, but are not limited to, different treatment modalities, field geometry settings for external beam radiotherapy, side effect predictions, organ and/or tumor segmentation, machine therapy attributes, dosage administration attributes (e.g., dosage amount), treatment frequency, treatment timing, monitored units, etc.

In some cases, the plan optimizer models 111 may correspond to particular radiotherapy clinics. For example, each of the plan optimizer models 111 may be trained based solely on training data generated at a particular clinic or may be trained to an accuracy threshold based on data from multiple clinics and then trained based on training data specific to a particular clinic. In some cases, the analytics server 110*a* may only provision or grant the radiotherapy clinics access to the plan optimizer models 111 for which the plan optimizer models 111 were trained. In some cases, the plan optimizer models 111 may be distributed or transmitted to the various radiotherapy clinics such as after the analytics server 110*a* determines the plan optimizer models 111 are accurate to an accuracy threshold.

The analytics server 110*a* may generate and display an electronic platform configured to use various computer models (including optimization algorithms and/or artificial intelligence and/or machine learning models) to automatically generate an optimized radiotherapy treatment plan according to an input set of objectives (e.g., minimum and/or maximum amounts of radiation different organs may receive during radiotherapy treatment). The electronic platform may include graphical user interfaces (GUI) displayed on each electronic data source 120 and/or the medical computing device 152. An example of the electronic platform generated and hosted by the analytics server 110*a* may be a web-based application or a website configured to be displayed on different electronic devices, such as mobile devices, tablets, personal computers, and the like. In a non-limiting example, a physician operating the physician device 120*b* may upload an image (e.g., a CT scan or another scan) to the analytics server 110*a* with a dose objective and/or radiotherapy treatment attributes via the electronic platform hosted by the analytics server 110*a*. The physician may also upload objectives (e.g., limits to the amount of radiation different OARs may receive) for the treatment. The analytics server 110*a* may execute the plan optimizer model 111 using the image, dose objective, and/or radiotherapy treatment attributes as an input and output predicted amounts of radiation that a PTV and surrounding OARs may receive as a result of treatment. The analytics server 110*a* may then use the systems and methods described herein to iteratively execute the plan optimizer model 111, adjusting the input parameters for each iteration to satisfy the input objectives, until the analytics server 110*a* generates an optimized radiotherapy treatment plan that best satisfies the input objectives (e.g., minimizes a cost function associated with the radiotherapy treatment plan), storing the results, weights, costs, and/or inputs of each iteration in memory for later retrieval if the physician seeks information about how the optimized radiotherapy treatment plan was generated.

The analytics server 110*a* may be any computing device comprising a processor and non-transitory machine-readable storage capable of executing the various tasks and processes described herein. Non-limiting examples of such computing devices may include workstation computers, laptop computers, server computers, and the like. While the system 100 includes a single analytics server 110*a*, the analytics server 110*a* may include any number of computing devices operating in a distributed computing environment, such as a cloud environment.

The analytics server 110*a* may execute software applications configured to display the electronic platform (e.g., host a website), which may generate and serve various webpages to each electronic data source 120. Different users may use the website to view and/or interact with predicted results from the plan optimizer models 111.

The analytics server 110*a* may be configured to require user authentication based upon a set of user authorization credentials (e.g., username, password, biometrics, cryptographic certificate, and the like). The analytics server 110*a* may access the system database 110*b* configured to store user credentials, which the analytics server 110*a* may be configured to reference in order to determine whether a set of entered credentials (purportedly authenticating the user) match an appropriate set of credentials that identify and authenticate the user.

The analytics server 110*a* may also store data associated with each user operating one or more electronic data sources 120. The analytics server 110*a* may use the data to weigh interactions while training various AI models accordingly.

For instance, the analytics server 110a may indicate that a user is a medical professional whose inputs may be monitored and used to train the machine learning models or other computer models described herein.

The analytics server 110a may generate and host webpages based upon a particular user's role within the system 100. In such implementations, the user's role may be defined by data fields and input fields in user records stored in the system database 110b. The analytics server 110a may authenticate the user and may identify the user's role by executing an access directory protocol (e.g. LDAP). The analytics server 110a may generate webpage content that is customized according to the user's role defined by the user record in the system database 110b.

The analytics server 110a may receive patient data (e.g., medical images, height, weight, diagnosis, age, equipment, etc.) and images such as CT scans from a user or retrieve such data from a data repository, analyze the data, and display the results on the electronic platform. For instance, in a non-limiting example, the analytics server 110a may query and retrieve medical images from the database 120d. The analytics server 110a may execute various models 111 (stored within the analytics server 110a) to analyze the retrieved data. The analytics server 110a may then display the results to be interacted with via the electronic platform on the physician device 120b, the medical device 150, and/or the medical computing device 152.

The electronic data sources 120 may represent various electronic data sources that contain, retrieve, and/or input data associated with a patient's treatment plan including patient data and treatment data. For instance, the analytics server 110a may use the clinic computer 120a, the physician device 120b, the server 120c (associated with a physician and/or clinic), the database 120d (associated with the physician and/or the clinic) to retrieve/receive data associated with a patient's treatment plan.

The electronic data sources 120 may also represent input/output devices that can receive inputs from a user (e.g., a physician) and transmit the inputs to the analytics server 110a. For example, a user may submit a query about an optimal radiotherapy treatment plan via a microphone 120e or another device such as using a touchscreen on a computer, a mouse, a joystick, a keyboard, or any other input/output device. In some cases, the user may hear playback of a spoken query through a speaker 120f to ensure the spoken query contains words or phrases as intended by the user.

The medical device 150 may be a radiotherapy machine (e.g., a linear accelerator, particle accelerator (including circular accelerators), or a cobalt machine) configured to implement a patient's radiotherapy treatment. The medical device 150 may also include an imaging device capable of emitting radiation such that the medical device 150 may perform imaging according to various methods to accurately image the internal structure of a patient. For instance, the medical device 150 may include a rotating system (e.g., a static or rotating multi-view system). A non-limiting example of a multi-view system may include stereo systems (e.g., two systems may be arranged orthogonally). The medical device 150 may also be in communication with a medical computing device 152 that is configured to display various GUIs discussed herein. For instance, the analytics server 110a may display the results predicted by the plan optimizer model 111 onto the medical computing device 152.

In operation, a physician may access an application executing on the physician device 120b and input radiotherapy treatment plan data (e.g., patient information, patient diagnosis, radiation therapy treatment attributes, etc.). The analytics server 110a may use a patient identifier to query patient data (e.g., patient anatomy and/or medical images) from the electronic data sources 120. The analytics server 110a may then utilize the systems and methods described herein to generate an optimized/uniform radiotherapy treatment plan according to a set of input objectives, present a radiation dose distribution on the physician device 120b being accessed by a physician, receive a query about aspects of the dose distribution from the computer device, answer the query using data generated from the output of the iterations of a computer model being executed in generating the optimized plan, and present the answer to the query on the physician device 120b.

In one example, the analytics server 110a may be in communication (real-time or near real-time) with the medical device 150. A server/computer hosting the medical device 150 can adjust the medical device 150 based on optimized radiotherapy treatment plan generated by the plan optimizer model 111. For instance, the analytics server 110a may execute the plan optimizer model 111 to generate attributes of an optimized radiotherapy treatment plan. The analytics server 110a may transmit instructions to the medical device 150 indicating how to operate the gantry and other field geometry settings for the medical device 150 according to the attributes of the optimized radiotherapy treatment plan to use to provide radiotherapy treatment to a PTV of a patient. The analytics server 110a may transmit instructions to the medical device 150 indicating any number or type of treatment attributes (e.g., field geometry settings) to facilitate such treatment based on the optimized radiotherapy treatment plan. In some cases, the analytics server 110a may transmit the radiotherapy treatment plan or the attributes of the radiotherapy treatment plan to the medical device 150 and the medical device 150 may treat the corresponding patient according to the attributes of the radiotherapy treatment plan and using intrinsic processes.

In some cases, instead of querying a query space to determine a response to a query, the analytics server 110a may query the external database 160. The external database 160 may be a database (e.g., a relational database) that stores previously optimized radiotherapy plans and/or the results and/or inputs of iterations of execution of a computer model that were used to generate such radiotherapy plans. The analytics server 110a may store the external database 160 or communicate with other computers, such as computers at radiotherapy clinics, to access and retrieve data from the database 160 stored in memory of the other computers.

In cases in which the analytics server 110a accesses the external database 160 to respond to a query, the analytics server 110a may search for results that were generated for optimized radiotherapy treatment plans similar to the optimized radiotherapy treatment plan the analytics server 110a generated for the patient (e.g., plans with a dose objective within a threshold, plans that are directed to curing a PTV in a similar area (e.g., within a threshold distance of each other with respect to a common point, such as the heart, of the patient) or of a similar size (e.g., a size within a threshold), etc.). In some cases, additionally or instead, the analytics server 110a may search for results that were generated for a patient with similar characteristics (e.g., same gender, heights within a threshold of each other, weights within a threshold of each other, etc.). The analytics server 110a may access the results associated with (e.g., generated during creation) such optimized radiotherapy treatment plans and retrieve data using the systems and methods described herein to respond to a query.

The external database 160 may store a computer model 162. The computer model 162 may be a computer model similar to the plan optimizer model 111. In some cases, the analytics server 110a may not generate the optimized radiotherapy treatment plan, but rather the computer storing the computer model 162 may generate the optimized radiotherapy treatment plan. In such cases, the analytics server 110a may transmit the image of the patient as well as the dose objective to the computer and the computer may perform the iterative process described herein using the computer model 162 to generate the optimized radiotherapy treatment plan. Accordingly, the analytics server 110a may retrieve the optimized radiotherapy treatment plan and aspects of the plan, such as a resulting dose-volume histogram (DVH) under the plan, from the computer and forward the plan and the aspects to the physician device 120b. The analytics server 110a may then operate as an intermediary server that facilitates communication between the physician device 120b and the computer storing the external database 160. Such a configuration may be advantageous if the computer model 162 is better trained (e.g., is trained to a higher accuracy) for generating optimized radiotherapy treatment plans or if the analytics server 110a is currently using computer resources to generate optimized radiotherapy treatment plans for other patients.

In a non-limiting example, the analytics server 110a may generate an adjustable optimized radiotherapy treatment plan. To do so, the analytics server 110a may retrieve one of the plan optimizer models 111 and an image of a patient (e.g., a CT scan, a PET scan, etc.) from the database 110b. The analytics server 110a may execute the plan optimizer model 111 using the image, a dose objective, and a set of attributes of a radiotherapy treatment plan to obtain an expected amount of radiation OARS and a PTV of the patient will receive under the plan. The analytics server 110a may compare the expected amounts to objectives input by a physician treating the patient. The analytics server 110a may determine the expected amounts do not satisfy the objectives and adjust the attributes of the radiotherapy treatment plan to better satisfy the objectives, storing the results of the output and/or the differences between the objectives and the expected values in the process. The analytics server 110a may iteratively perform this process until identifying a converged "optimized" radiotherapy plan to treat the patient and presenting the optimized plan to the physician.

Upon viewing the optimized plan, the physician may submit a query (e.g., via the physician device 120b) to the analytics server 110a asking for information about the optimized plan. The query may be a question such as "Why is this objective not met?", "What objectives can be changed to reduce the amount of radiation the liver receives?", "Provide me with a summary of this radiotherapy treatment plan," etc. The analytics server 110a may receive such queries and identify query terms from the queries (e.g., use natural language processing techniques to identify keywords in the queries or identifying the input values of the queries). The analytics server 110a may use the query terms to query the query space for data to answer the question. The analytics server may identify data that can answer the question from the query space and generate a response to the query with the identified data. In one example, the response may include an identification of an organ and an indication of whether to increase or decrease the maximum or minimum dosage of radiation that the organ can receive during treatment. The analytics server may transmit the response to the physician device 120b with instructions for the response to appear on a user interface being displayed on the physician device 120b.

In some cases, the physician may submit a query to generate a new radiotherapy treatment plan to satisfy a new set of objectives (e.g., a set of objectives with at least one adjustment or new objective as compared to the set of objectives the previously optimized radiotherapy treatment plan was based on). For instance, the physician may transmit an indication to increase the maximum limit of radiation the lungs may receive during treatment. In receiving the query, the analytics server 110a may perform the iterative process of executing the plan optimizer model 111 to determine a new optimized radiotherapy treatment plan for the adjusted objectives, storing the results of each iteration in the query space. The analytics server 110a may identify a new radiotherapy treatment plan and generate a new DVH for the plan. The analytics server 110a may then transmit the new DVH to the physician device 120b with instructions to display the new DVH.

Figure 2:
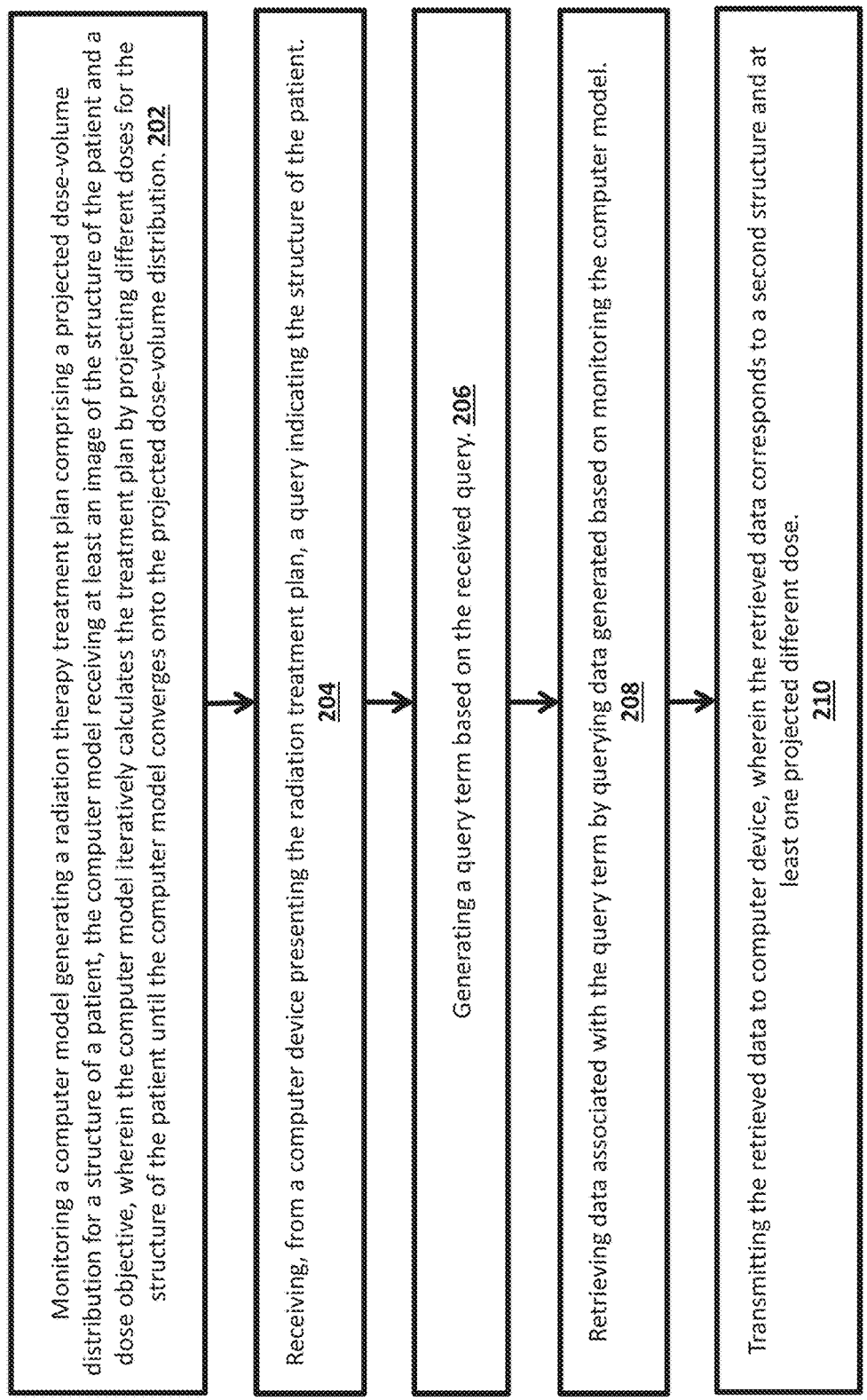
FIG. 2 illustrates a flow diagram of a process executed in a radiotherapy treatment plan system, according to an embodiment.

FIG. 2 illustrates a flow diagram of a process executed in a radiotherapy treatment plan system, according to an embodiment. The method 200 may include steps 202-210. However, other embodiments may include additional or alternative steps, or may omit one or more steps altogether. The method 200 is described as being executed by a data processing system (e.g., a computer similar to the analytics server 110a or the data source 120, as described with reference to FIG. 1). However, one or more steps of the method 200 may be executed by any number of computing devices operating in the distributed computing system. For instance, one or more computing devices may locally perform part or all of the steps described in FIG. 2 or a cloud device may perform such steps.

In step 202, the data processing system may monitor a computer model. The computer model may be a plan optimizer model including an optimization algorithm and/or a machine learning model (e.g., a neural network, random forest, a support vector machine, etc.) that the data processing system executes to generate a radiotherapy treatment plan (e.g., an optimal radiotherapy treatment plan) using a dose objective and/or an image (e.g., a contoured image) as input. The data processing system may also include different radiotherapy treatment plan attributes as input into the plan optimizer model. During execution, the plan optimizer model may output an expected radiation dosage that different organs surrounding a PTV or a target organ (e.g., an organ with a tumor receiving treatment under the radiotherapy treatment plan) will receive during treatment by a radiotherapy machine based on the radiotherapy treatment plan attributes. A physician may evaluate the output and determine if the radiation dosage that the organs surrounding the PTV are projected to receive is acceptable. If the physician determines the output is not acceptable, the physician may input a different set of radiotherapy treatment plan attributes (e.g., adjust the radiotherapy treatment plan attributes) to obtain a new output. For each output expected radiotherapy dosage by the computer model, the data processing system may store the expected dosage for each OAR and the PTV in a query space (e.g., in a database, buffer, or cache in memory), thus monitoring the computer model for the different outputs. Accordingly, if the physician later seeks to view which set of radiotherapy treatment plan attributes correspond to which results, the data processing system may quickly retrieve the stored results from the query space in memory to provide to the physician.

In some cases, the data processing system may monitor the computer model as the computer model automatically converges on radiotherapy treatment plan attributes that best satisfy input objectives for the different OARs. For example, a physician may input objectives that indicate a maximum dosage of radiation OARs that the physician finds acceptable when treating a PTV. The physician may also input weights for the objectives indicating an importance of satisfying the objectives. The data processing system may execute the computer model using an image, a dose objective, and/or radiotherapy treatment plan attributes as input. In doing so, the computer model may output an expected radiation dosage the OARs would likely receive from a radiotherapy machine operating with the radiotherapy treatment plan attributes. The data processing system may compare the output to the input objectives to identify differences between the output and the respective input objectives. If an expected or projected radiation dosage for an OAR exceeds an input objective limit for the OAR, the data processing system may adjust the radiotherapy treatment plan attributes and/or the weights of the objectives and execute the computer model again but with the adjusted radiotherapy treatment plan attributes. The data processing system may repeat this process until converging on radiotherapy treatment plan attributes that most closely satisfy the input objectives (e.g., minimize a loss function for the image and dose objective), storing the output for each iteration in the query space in memory. More detail about how the computer model converges on an optimal radiotherapy treatment plan is described in U.S. patent application Ser. No. 17/036,176, filed Sep. 29, 2020, the entirety of which is incorporated by reference herein. In this way, the data processing system may automatically monitor a computer model as the computer model converges onto an optimal radiotherapy treatment plan.

The image the data processing system may input into the computer model may be a two-dimensional or a three-dimensional image and may include pixels or voxels, respectively. The image may be a CT or a PET scan of an individual that is receiving radiotherapy treatment at one or more radiation therapy clinics. The image may depict the organs and/or bone structure of the individual and may be contoured to indicate the individual organs or structures of the patient and/or labeled to indicate the targeted area for receiving treatment (e.g., a tumor may be labeled as being a tumor or an area receiving treatment).

The data processing system may execute the computer model using the received image from a radiotherapy clinic. In one example, the data processing system may receive the image responsive to an individual (e.g., a technician or a doctor) uploading the image to a database of the data processing system. For instance, the physician may capture a CT scan (e.g., using a CT scanner at a radiotherapy clinic) and upload the scan to the data processing system. The physician may upload the scan manually through a user selection at a user interface or the scanner may automatically upload the image.

In some cases, the output of the computer model is a dose-volume histogram (DVH). The dose-volume histogram may be a histogram graph that illustrates the amount of radiation percentages of different organs are projected to receive while receiving treatment by a radiotherapy machine given a certain set of radiotherapy treatment attributes. For example, the dose-volume histogram may have an x-axis with increasing amount of radiation that organs may receive under the radiotherapy treatment plan and a y-axis indicating the volume (e.g., percentage) of an organ that will receive the respective amounts of radiation. The dose-volume histogram may include one or more lines that correspond to different organs and that indicate the volumes of the organs that will receive different amounts of radiation. A physician may view the dose-volume histogram to determine if different organs are receiving acceptable amounts of radiation under a particular treatment plan.

In some cases, to aid a physician, a DVH may include indicators that indicate the objectives the physician input to the data processing system. The physician may view the indicators on a converged DVH to view how well a converged (e.g., optimized) radiotherapy treatment plan satisfies the input objectives. Accordingly, the physician may determine if the input objectives enable OARs to receive acceptable radiation or if the physician needs to adjust the input objectives to make the treatment safer (e.g., increase or decrease the radiation one OAR may receive under an objective to increase or decrease the radiation another OAR may receive).

In some embodiments, the data processing system may execute the computer model based further on a monitored unit (MU) parameter. The monitored unit parameter may be a maximum amount of radiation the physician is comfortable with the patient receiving under the radiotherapy treatment plan. The monitored unit parameter may include a maximum amount of radiation the patient may receive in the aggregate and/or maximum amounts of radiation different percentages of the patient may receive under the radiotherapy treatment plan. The monitored unit parameter may be an input into the computer model such that the computer model may perform its calculations without violating the monitored unit parameter (e.g., perform each calculation avoiding values that correspond to emitting more radiation than the monitored unit parameter). Accordingly, the computer model may calculate an optimized radiotherapy treatment plan that would not result in overdosing the patient with radiation.

In some cases, the computer model converges onto a projected dose-volume distribution (e.g., a DVH) and the monitored unit parameter using a cost function. For example, the computer model may assign costs to the objectives (e.g., the costs of satisfying the objectives) or the organs that will receive radiation under the radiotherapy plan. As the data processing system executes the computer model in different iterations in accordance with the objectives input by the physician and the MU parameter, the data processing system may adjust radiotherapy treatment plan attributes to satisfy the different objectives and the MU parameter. As the computer model targets satisfying the different objectives and the MU parameter, the data processing system may assign the cost of satisfying the objectives and the MU parameter to the objectives and the MU parameter. The computer model may assign costs to the objectives in memory with associations with the corresponding organs as well as the costs of satisfying the MU parameter. The computer model may converge onto the projected dose-volume distribution with or without the MU parameter.

In some cases, the output of the computer model is not a dose-volume histogram. For instance, the computer model may output other numerical or other visual indicators of the amount of radiation the PTV and the OARs will receive. For example, the output may be or include the data of a dose-volume histogram in sentence or an otherwise descriptive form or the output may be colors of colors on a red to blue scale indicating the amount of radiation each PTV and OAR will receive as compared to each other. The computer model may output any type of such projected dose-volume distribution to indicate to a physician the amount of radiation individual organs or other structures may receive under a radiotherapy treatment plan.

For each iteration of executing the computer model to generate the converged radiotherapy treatment plan, the data processing system may store the output radiation dosage (or the data of an output DVH) in the query space in memory (or in an externally stored database). In some cases, the data processing system may store the output radiation dosage, cost function data (e.g., the cost of the iteration), the weights that were used to generate the output radiation dosage, etc., in a buffer or cache in memory for quick retrieval. In some implementations, the data processing system compare the outputs between iterations and determine correlations between increasing or decreasing the amount of radiation different organs receive (e.g., a decrease in radiation to one organ may cause an increase in radiation to another organ) and store the correlations. The data processing system may store such data for each iteration in a separate file. For instance, the data processing system may store the above data and any additional data related to the iteration, such as which attributes were accepted and rejected, the reasons for the acceptances and rejections, a timestamp of when the iteration was performed, the time the iteration took to complete, the loss function itself, the effort for the iteration, etc. The data processing system may store the data in groups (e.g., in rows of a database) with identifiers (e.g., numeric or alphanumeric identifiers) indicating the execution iterations from which the data was generated. The data processing system may increment and store the identifiers for each iteration to enable the data for each iteration to be separately stored and retrieved together. Accordingly, if the data processing system receives a query from a physician asking for data pertaining to a particular iteration, the data processing system may identify the requested data and use the identifier and/or other storage mechanism (e.g., identify data in the same row or the same file) to retrieve all of the data pertaining to the particular iteration.

In storing the data for a converged radiotherapy treatment plan, the data processing system may store the data with an identifier of the patient receiving treatment and/or another identifier (e.g., a numeric or alphanumeric identifier) that uniquely identifies the treatment with the converged radiotherapy treatment plan. By doing so, the data processing system may store the data such that a physician may later search the patient's plan by name and/or by the identifier to view the risks of overdosing an OAR of the patient with radiation during treatment.

In step 204, the data processing system may receive a query indicating a structure (e.g., an organ, bone, or another body part) of the patient. The data processing system may receive the query from a computer device presenting the converged results output (e.g., the converged DVH for an optimized radiotherapy treatment plan) on a user interface. For example, the data processing system may transmit a user interface containing a converged DVH generated by the computer to a computer device being accessed by a physician. The computer device may receive the user interface containing the converged DVH and present the user interface on a display. The physician accessing the computer device may view the user interface containing the converged DVH. Upon viewing the user interface, the physician may analyze the DVH to determine if the DVH indicates the PTV and the OARs adjacent to or surrounding the PTV are projected to receive an acceptable amount of radiation under the radiotherapy treatment plan that corresponds to the converged DVH. If the physician identifies an OAR that is receiving too much (or too little) radiation under the radiotherapy treatment plan, the physician may provide an input to the computer device displaying the user interface to transmit a query for data about the OAR.

The physician may provide an input to the computer device displaying the user interface in a few manners. For instance, in some cases, the physician may select a portion of the DVH using a mouse, touchpad, or some other input device that corresponds to a volume percentage of an organ that receives too much radiation (e.g., a portion on the line representing the projected radiation the organ will receive exceeds or is less than an input objective for the organ). In such cases, the computer device will transmit an indication of the selected portion (e.g., the coordinates on the DVH, an identification of the selected organ, the selected volume, the selected radiation dosage, etc.). In other cases, the physician may input a query by speaking into a microphone of the computer device. For instance, the physician may ask a question such as "Why is the liver receiving so much radiation?", "Why aren't the input radiotherapy treatment plan objectives for the bladder or the pancreas met?", "How can we reduce the radiation the lungs will receive?", etc. The microphone may capture the sound waves and either directly transmit the sound waves (e.g., binary or analog values representing the sound waves) to the data processing system or use natural language processing techniques locally to identify the question (e.g., identify the entities, utterances, and/or the intent of the spoken phrase against words in a local database) and transmit the results to the data processing system. In yet other cases, the computer device may present a list of template questions or statements about the DVH from which the physician may select one of the templates. The computer device may then transmit the selected template to the data processing system for further processing.

In step 206, the data processing system may generate a query term based on the received query. The query term may be a value containing one or more words or phrases that the data processing system may use as a key in a search through the output results generated by the computer model creating the converged DVH. The data processing system may generate the query term in different manners depending on the format in which the data processing system received the query. For instance, in cases in which the data processing system receives a selection from the user interface by an input/output device, the data processing system may generate the query term by retrieving the identification of the selected organ, radiation dosage, and/or volume from the data packet containing the selection. The retrieved data may be the query term. In cases in which the data processing system receives data representing sound waves (e.g., data representing sound waves spoken by a physician), the data processing system may generate the query term by executing a natural language protocol on the sound wave data to identify entities, utterances, and/or intents and identify words or phrases based on the entities, utterances, and/or intents from a database. The data processing system may use the identified words or phrases to query the query space in memory containing the results generated by the computer model. In instances in which the data processing system receives selected phrases or terms generated using natural language processing techniques by the computer device, the data processing system may identify the terms in the phrases or the terms generated using natural language processing techniques to use to query the query space. In this way, the data processing system may generate a query term, or a key, to use to search the query space in response to a query by a physician regarding the results output by the computer model.

In step 208, the data processing system may retrieve data associated with the query term by querying data generated based on monitoring the computer model. The data processing system may query data generated based on monitoring the computer model by identifying the costs of satisfying the different objectives that the computer model used in generating the converged DVH. For example, the data processing system may receive a question and/or generate a query term for a question asking why the radiation dosage for the bladder was too high. Upon generating the query term, the data processing system may search the query space for data indicating the cost values of adjusting the dosage the bladder received for different OARs and/or the PTV. The cost values may be stored values for the different organs (e.g., values indicating the importance of protecting the specific organs) or values generated by the computer model during execution based on the proximity or location of the organ as compared to the PTV, the size of the respective organs, the health (e.g., a predefined value indicating the health) of the organs, the difficulty of reducing the radiation below the input objectives for the organs, etc. The data processing system may identify the costs and identify the lymph nodes, for example, as being associated with the highest cost (e.g., the most difficult organ for which to reduce the radiation below the input radiotherapy treatment plan objective). Based on this identification, the data processing system may generate an answer indicating the reason the radiation dosage for the bladder was too high is because the computer model adjusted the radiotherapy plan attempting to ensure the radiation the lymph nodes received met the input radiation limits for the lymph nodes. In this example, the data processing system may quickly determine the organs associated with lower costs did not cause the queried organ to project to receive too much radiation because the computer model may have quickly determined the radiotherapy treatment plan attributes to avoid violating any input radiation limits for the lower costs organs.

In another example, the data processing system may query and retrieve data from a matrix in the query space. The matrix may be a matrix that stores correlation values indicating the correlations in the amount of radiation individual organs are projected to receive as a result of adjusting the amount of radiation other organs receive. For example, as the computer model iteratively adjusts the radiation treatment plan attributes to identify the optimal attributes to meet the input objectives, the data processing system may identify the cost values of satisfying the objectives that change as the result of a change in cost value for another objective (e.g., a downward change in a cost value for one organ may result in an upward change in a cost value for another organ). In some cases, additionally or instead, the data processing system may identify positive or negative or negative correlations in the amount of radiation one OAR receives as a result of a change in the amount of radiation another OAR receives. The data processing system may identify and store such correlations in a matrix data structure with indications of the organs that correspond to the objectives in the query space. Accordingly, if the data processing system receives a query asking how to reduce or increase the amount of radiation one OAR will receive, the data processing system may identify a positive or negative correlation the OAR has with another OAR from the matrix and respond with an indication to increase or decrease, respectively, the radiation limit for the correlated OAR.

In yet another example, the data processing system may use a set of rules to retrieve data associated with the query term, such as to retrieve indications of conflicts. For example, the data processing system may receive a question asking why an OAR is receiving too much radiation. As may be illustrated on the image of the patient, the OAR may be overlapping, directly adjacent to, or touching the PTV. The data processing system may analyze the image and determine the distance between the OAR and the PTV (e.g., the outlines of the OAR and the PTV) is less than a defined threshold. Responsive to the determination, the data processing system may generate a response indicating that because the two organs are so close or overlapping, there is a conflict and the computer model could not generate a radiotherapy treatment plan that decouples the amount of radiation each organ receives or that could reduce the amount of radiation the OAR receives while ensuring the PTV receives the requisite radiation to reduce the size of the tumor. In another example, the data processing system may receive a query asking for the number of conflicts there are under the radiotherapy treatment plan. Upon receiving the query, the data processing system may maintain and increment a counter for each conflict the data processing system identifies using the set of rules. The data processing system may retrieve the count of the counter in response to receiving such a query.

At step 210, the data processing system may transmit a message containing the retrieved data to the computer device. In doing so, for example, the data processing system may transmit a message indicating to change the acceptable dosage limit in an OAR so the radiotherapy treatment plan may cause the queried OAR to receive an amount of radiation below the indicated limit for the organ. For example, the data processing system may receive a query asking how to reduce the amount of radiation a person's lung will receive while undergoing radiotherapy treatment. The data processing system may query the query space containing the results of each iteration of executing the computer model and retrieve data indicating the bladder has an inverse (or negative) relationship with the lung. Accordingly, the data processing system may transmit an indication of the bladder to the computer device. The data processing system may transmit the indication with instructions to display the indication of the bladder on the user interface (e.g., in a separate window on the user interface) being presented on the computer device. Based on the displayed indication, the physician accessing the computer device may determine that to lower the radiation the lungs will receive, the physician may increase the limit on the amount of radiation the bladder can receive during treatment.

In some cases, the data processing system may additionally query the query space for an indication of the projected dose for which a radiation limit needs to be adjusted. For instance, continuing with the example above, the physician may have input separate radiation dose limits (or objectives) for different percentages of the lung. In submitting a query, the physician may indicate one of the limits (either in the physician's speech or using an input/output device). The data processing system may use the indicated limit as a query term when querying the query space (e.g., query the query space for which other organs have a high cost or negative correlation with the organ at the selected dosage amount). The data processing system may identify the organ for which a limit can be adjusted to reduce the amount of radiation an indicated organ will receive for a given volume percentage of the organ and the limit itself, and transmit an indication of the organ and, in some cases, the limit back to the computer device for display to the physician.

In one example, the data processing system may receive a query for information about a particular objective for an organ. For example, the data processing system may receive a query about a dosage limit for a bladder of a patient and why the projected dosage for the bladder exceeds the dosage limitation. The data processing system may receive the request as a question such as, for example, "show me the iteration history for minimizing the amount of radiation the bladder will receive under the plan." In response to such a request, the data processing system may retrieve data from different iterations that were performed in an attempt to lower the amount of radiation the bladder would receive under the optimal radiotherapy plan to show why the amount of radiation could not be lowered without substantially impacting the amount of radiation other organs received under the plan. The data processing system may transmit the retrieved data to the computer device in response to the query to illustrate to the physician why the amount of radiation could not be significantly lowered.

In another example, the data processing system may receive a query asking how to adjust the objectives such that a current unmet objective under the radiotherapy treatment plan may be met. After receiving such a query, the data processing system may iteratively execute the computer model, in some cases increasing a weight associated with the organ associated with the unmet objective in a cost function, until the data processing system identifies a new optimized radiotherapy treatment plan that satisfies the previously unmet objective. The data processing system may then transmit the new objectives to the computer that transmitted the query to the data processing system for display to show the physician how to adjust the objectives to ensure the unmet objective is met.

Figure 3:
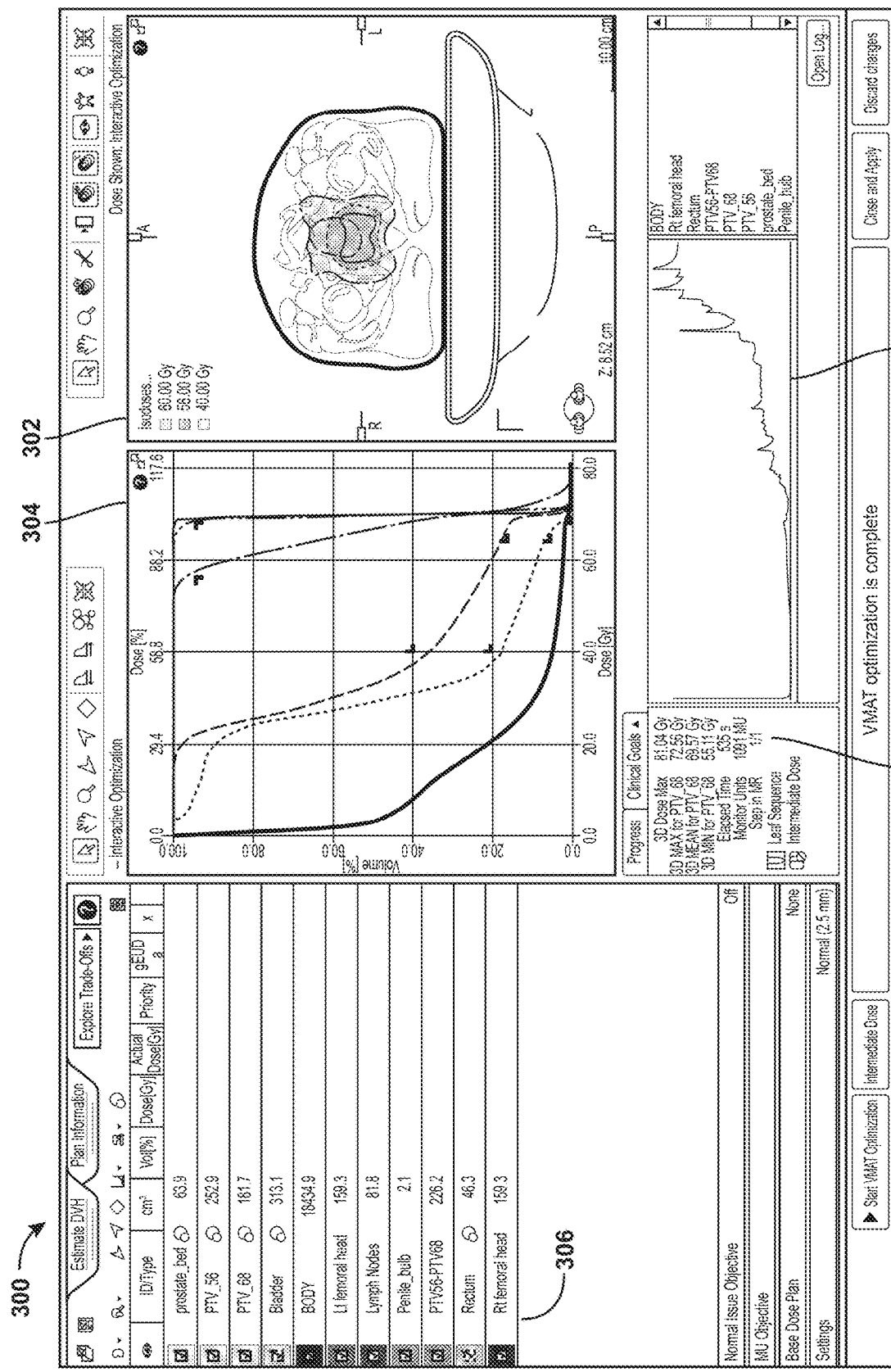
FIG. 3 illustrates a user interface of a converged radiotherapy treatment plan, according to an embodiment.

FIG. 3 illustrates a user interface 300 of a converged radiotherapy treatment plan, according to an embodiment. The user interface 300 may include a contoured image 302, a DVH 304, a list of organs 306, a cost function graph 308, and a radiotherapy plan dosage characteristics 310, among other features. A data processing system (e.g., a computer similar to the analytics server 110a or the data source 120, as described with reference to FIG. 1) may generate the user interface 300 after receiving the contoured image 302 and a dose objective for a PTV and/or one or more OARs and iteratively executing a computer model to determine an optimized radiotherapy treatment plan with the lowest cost (e.g., the radiotherapy treatment plan that most closely follows the dose objectives) according to the systems and methods described herein. The data processing system may generate the DVH 304 to illustrate the amount of radiation individual organs will receive under the optimized radiotherapy treatment plan where each line represents a histogram for a different organ. The DVH 304 may also include the radiation dose limits for the individual organs, which are indicated by colored markers in the DVH 304. The colors of the radiation dose limits may match the colors of the lines that correspond to the same organs to indicate the lines with which the limits are associated. The data processing system may generate the user interface 300 and transmit the user interface 300 to a computer device with instructions to display the user interface 300 on the computer device for evaluation by a physician.

The cost function graph 308 may indicate the cost function of the converged radiotherapy treatment plan illustrated in user interface 300. The cost function may include values of the total cost of the radiotherapy treatment plan for each iteration that the data processing system executes a computer model. As illustrated, the cost function may begin with a sharp decrease towards zero as the computer model adjusts attributes of the radiotherapy treatment plan to satisfy the physician initial input objectives. The cost function may then start to increase as the physician inputs different objectives or adjusts the weights that correspond to different objectives or organs and submits queries with new objectives or attributes that cause the cost function to vary. The cost function graph 308 may be useful to a viewing physician to see the effects of the varied objectives or the changes in the weights of the objectives or organs.

The radiotherapy plan dosage characteristics 310 may include statistics regarding the amount of radiation a person's body or structures within the person's body would receive under the converged radiotherapy treatment plan. The radiotherapy plan dosage characteristics 310 may include values for the maximum amount of radiation the patient's body will receive, the maximum amount of radiation the PTV would receive, the average amount of radiation the PTV will receive, the minimum amount of radiation the PTV will receive, the length of the time the computer model ran to generate the radiotherapy treatment plan, and the number of monitored units the radiotherapy machine is projected to emit under the plan. The radiotherapy plan dosage characteristics 310 may include any number of statistics of any type.

Figure 4:
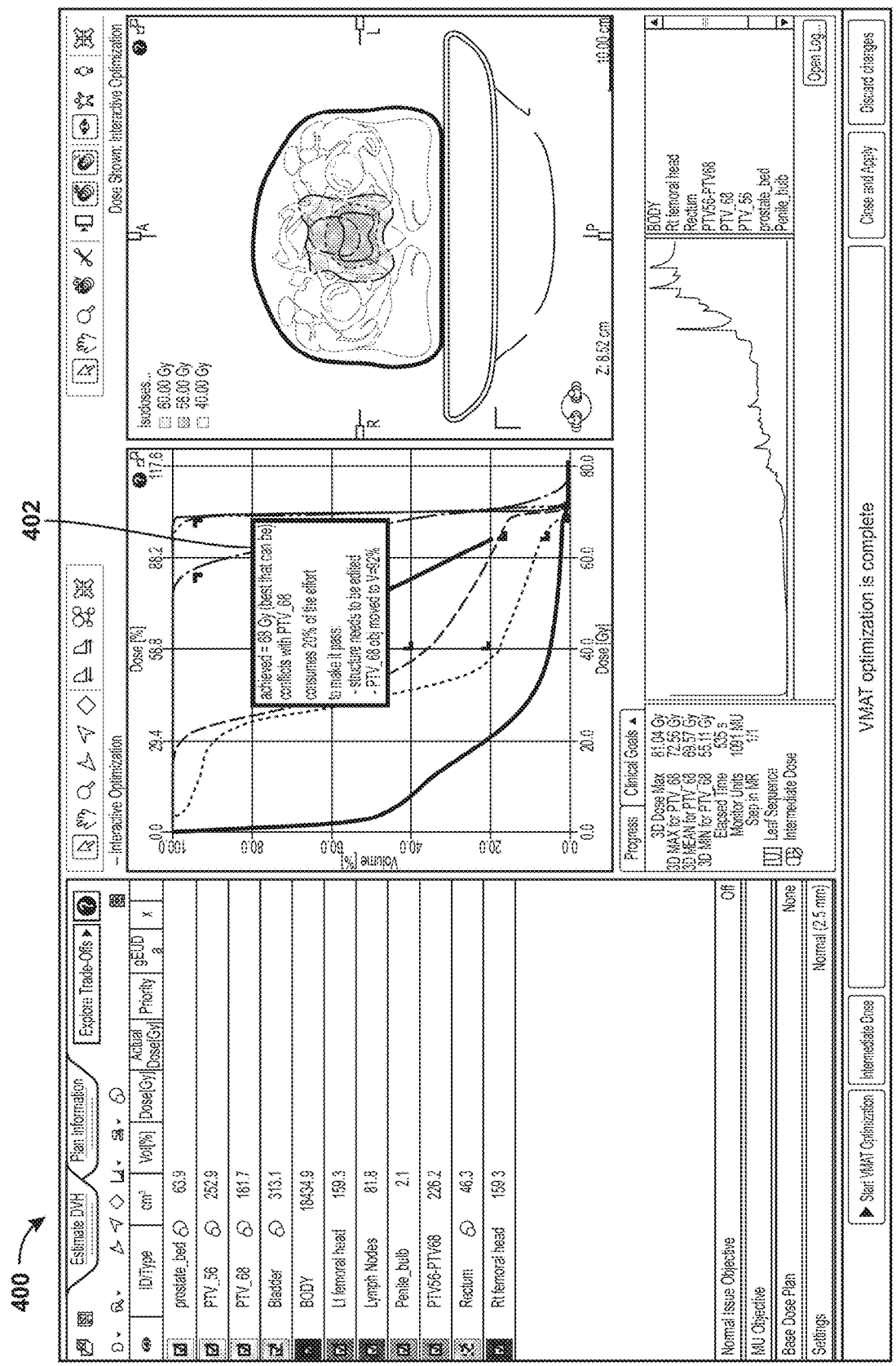
FIG. 4 illustrates a user interface of an inspection of a converged radiotherapy treatment plan, according to an embodiment.

FIG. 4 illustrates a user interface 400 including an inspection of a converged radiotherapy treatment plan, according to an embodiment. The user interface 400 may be similar to or the same as the user interface 300, shown and described with reference to FIG. 3. A data processing system (e.g., a computer similar to the analytics server 110a or the data source 120, as described with reference to FIG. 1) may generate the user interface 400 after receiving a query from a computer device displaying the user interface 300. The query may be a request regarding why a portion of the bladder is projected to receive an amount of radiation above an input dosage limit and/or how to resolve the problem. In response to receiving the query, the data processing system may generate a query term based on the query and use the query term to query a query space containing the results of each iteration of execution by the computer model, as described herein. Based on the query, the data processing system may determine there is a conflict with the PTV that made it very difficult to impossible to reduce the amount of radiation the bladder is projected to receive (e.g., the PTV needs to receive a specific dosage of radiation for adequate treatment, so that dosage cannot be lowered to reduce the amount of radiation the bladder would receive). The data processing system may then generate the user interface 400 with a separate window 402 that contains text indicating the conflict.

In some cases, as illustrated, the data processing system may include other information about why the objective dosage limit for the bladder was not met in the window 402. For example, the data processing system may include information about the amount of effort (e.g., percentage of iterations) the computer model put into ensuring the dosage limit was met for the bladder at the specified volume. The data processing system may also include information about how the physician can adjust the radiotherapy treatment plan to ensure the dosage limit was met.

Figure 5:
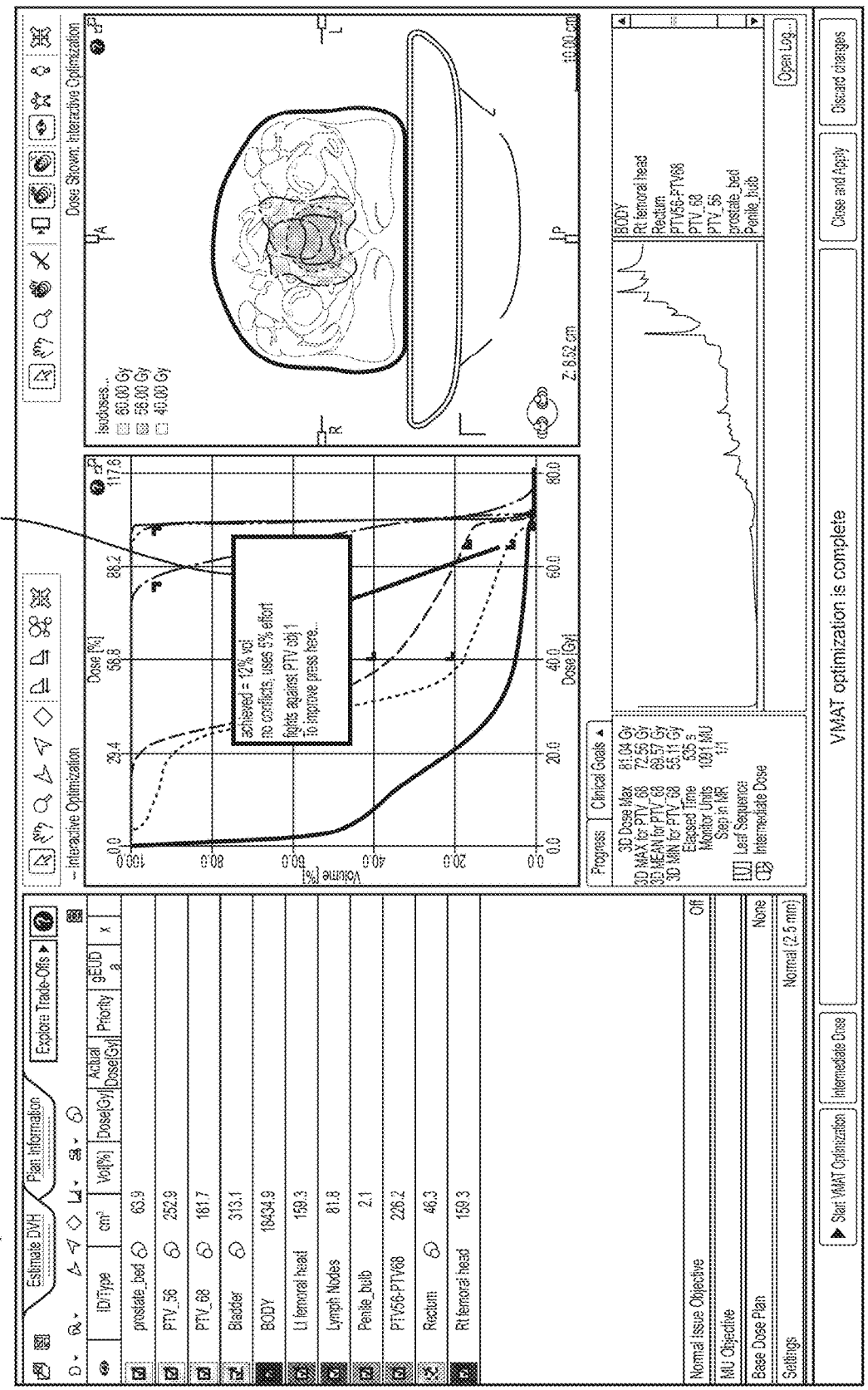
FIG. 5 illustrates a user interface including a dialogue box to improve a converged radiotherapy treatment plan, according to an embodiment.

FIG. 5 illustrates a user interface 500 including a dialogue to improve a converged radiotherapy treatment plan, according to an embodiment. The user interface 500 may be similar to or the same as the user interface 300, shown and described with reference to FIG. 3. A data processing system (e.g., a computer similar to the analytics server 110a or the data source 120, as described with reference to FIG. 1) may generate the user interface 500 after receiving a query from a computer device displaying the user interface 300. The query may be a request for information about why a portion of the rectum is projected to receive an amount of radiation that satisfies the input dosage limit for the rectum. In response to receiving the query, the data processing system may generate a query term based on the query and use the query term to query a query space containing the results of each iteration of execution by the computer model, as described herein. Based on the query, the data processing system may determine there are not any conflicts with other organs that caused the selected dosage limit for the rectum to be exceeded. Based on the query, the data processing system may also determine only 5% effort was used to satisfy the dosage limit and that there is a negative correlation between the radiation dosage the rectum receives and the radiation dosage the PTV receives. The data processing system may then generate the user interface 500 with a separate window 502 that contains text indicating this information. In this way, the data processing system may generate a window with a dialogue to show a physician information indicating why a particular dosage limit or objective was met and/or ways to further improve or decrease the amount of radiation an organ receives.

Figure 6:
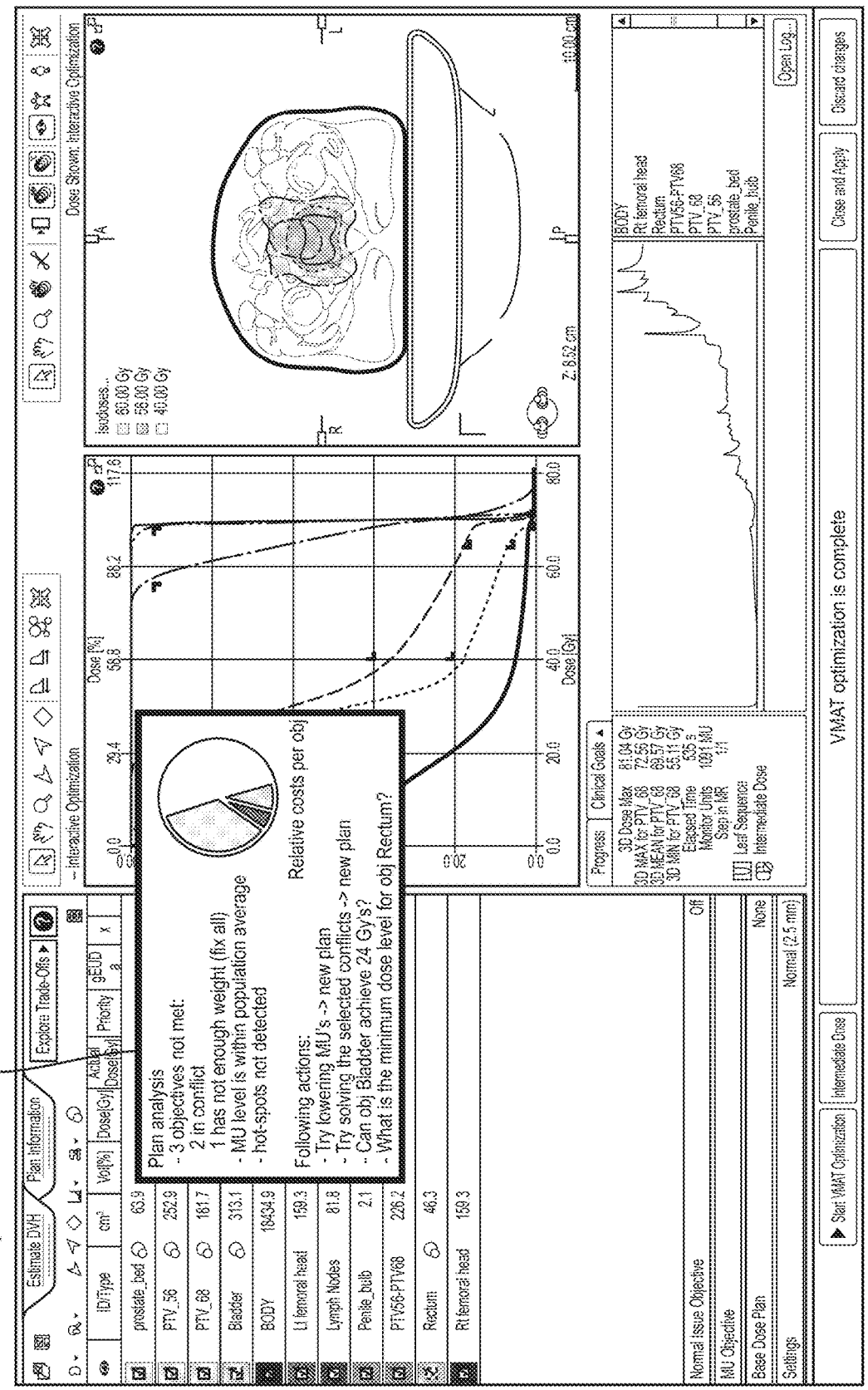
FIG. 6 illustrates a user interface including an analysis of a radiotherapy treatment plan, according to an embodiment.

FIG. 6 illustrates a user interface 600 including an analysis of a radiotherapy treatment plan, according to an embodiment. The user interface 600 may be similar to or the same as the user interface 300, shown and described with reference to FIG. 3. A data processing system (e.g., a computer similar to the analytics server 110a or the data source 120, as described with reference to FIG. 1) may generate the user interface 600 after receiving a query from a computer device displaying the user interface 300. The query may be a request for an analysis of the radiotherapy treatment plan based on the multiple iterations the computer model performed in generating a converged radiotherapy treatment plan. In response to receiving the query, the data processing system may generate a query term based on the query and use the query term to query a query space containing the results of each iteration of execution by the computer model, as described herein. Based on the query, the data processing system may determine the number of objectives (e.g., dosage limits) that were not met, the MU level of the plan as compared to a similar population, the number of hot-spots that result from the plan, etc. The data processing system may also determine the reasons the objectives were not met as well as recommendations to improve the plan. The data processing system may then generate the user interface 600 with a separate window 602 that contains text (e.g., a sentence in a natural language, such as English) indicating the determined data about the radiotherapy treatment plan and the iterations of execution of the computer model performed to generate the converged plan. Natural language may mean a language that has developed naturally in use (as contrasted with an artificial language or computer code). The separate window 602 may also include a chart (e.g., a pie chart) that illustrates the relative costs of the different objectives the physician input into the data processing system.

FIG. 7 illustrates another flow diagram of a process executed in a radiotherapy treatment plan system, according to an embodiment. The method 700 may include steps 702-706. However, other embodiments may include additional or alternative steps, or may omit one or more steps altogether. The method 700 is described as being executed by a data processing system (e.g., a computer similar to the analytics server 110a or the data source 120, as described with reference to FIG. 1). However, one or more steps of method 700 may be executed by any number of computing devices operating in the distributed computing system. For instance, one or more computing devices may locally perform part or all of the steps described in FIG. 7 or a cloud device may perform such steps.

In step 702, the data processing system may monitor a computer model. The computer model may be an analytical model (e.g., an optimization algorithm) or a machine learning model (e.g., a neural network, random forest, a support vector machine, etc.) that the data processing system executes to generate a radiotherapy treatment plan (e.g., an optimal radiotherapy treatment plan) using a dose objective and an image (e.g., a contoured image) as input. The data processing system may monitor the computer model similar to how the data processing system monitors the computer model in step 202, shown and described with reference to FIG. 2.

In step 704, the data processing system may receive a query indicating a structure (e.g., an organ) of the patient and a new objective of the radiation therapy treatment plan. The data processing system may receive the query in response to a presentation of the radiation therapy treatment plan by a computer device. The new objective may be a new dosage limitation or objective for an organ or an adjustment to a dosage limitation or objective that the computer model used to generate the current optimized plan. For example, the data processing system may receive a query from a computer device in which a physician asked what would the impact be of ensuring 15% of a patient's bladder does not receive more than 68 grays of radiation. The data processing system may receive the query as a string of text (e.g., a spoken phrase or a selected template). In response to receiving the query, the data processing system may identify the structure identified in the query, such as by using natural language processing techniques, or from data the computer device that transmitted the query extracted from text using natural language processing techniques. The data processing system may also identify the new objective from the query itself.

In step 706, the data processing system may instruct the computer model to execute a simulation of an additional iteration using the new objective. In doing so, the data processing system may update the radiotherapy plan attributes or weights of the organs or objectives the data processing system had previously determined optimally met the radiation dosage limitations or objectives for the patient's organs. The data processing system may update the radiotherapy plan attributes such that the projected radiation the PTV and/or OARs receive more closely match the new objective (e.g., add the new objective to the previously input objectives or replace an existing objective with the new objective). The data processing system may iteratively execute the computer model according to the new objective until the new objective is satisfied and the data processing system has identified an optimal radiotherapy plan. Upon identifying such a plan, the data processing system may generate DVH for the plan and transmit a user interface containing the DVH to the computer device that sent the query identifying the structure and the new objective to the data processing system.

In some cases, when generating the new optimal radiotherapy treatment plan to account for the new objective, the data processing system may update the cost function to illustrate the cost of the new plan as compared to the total cost of the plan in previous iterations. For example, as the data processing system executes the computer model to determine a new optimal radiotherapy treatment plan with the new objective, the data processing system may calculate the total cost (e.g., the cost function parameter) for each iteration. The data processing system may concatenate the new values for the total cost to the cost values that were generated when creating the previous plan. The concatenated values may illustrate the changes in cost of the plan and, effectively, the computer's view of how the plan performs compared to other iterations. Accordingly, the data processing system may create a graph of a cost function that the physician may view on a user interface to view an objective measure of how the radiotherapy plan performs after different adjustments and new objectives that the physician submits over time.

In one example, the data processing system may use perturbed optimization to a query. For instance, a user may request to know more about what happens to information in a radiation dose when an objective for a new structure is added. When adding the new structure, the data processing system may generate a new cost function term and execute the plan optimizer model to converge to a new radiotherapy treatment plan based on the new cost function term.

In some cases, the data processing system may calculate differences between the initial optimal radiotherapy treatment plan and the subsequent optimal radiotherapy treatment plan the data processing system calculated based on the new objective. The data processing system may do so, for example, by comparing the costs of the two plans and identifying the difference in the costs, comparing the amount of radiation individual organs receive in the aggregate or on an individual organ basis, comparing the number of objectives that were met under each plan, comparing the amount of time that is required for a radiotherapy session under each plan, etc., or any combination thereof. In some cases, the data processing system may overlay the DVH for each optimized radiotherapy plan to provide a juxtaposition between the two plans to the requesting physician. The data processing system may determine differences between the two plans based on any combination of these factors and transmit the differences to the computer device that submitted the query with the new objective.

In a non-limiting example, a computer implementing the systems and methods described herein may automatically gather information from trade-offs and correlations between the objectives input by a physician for a radiotherapy treatment plan. The computer may gather the information in a few manners: a) use straight-forward analytical calculations (e.g., calculating what objectives conflict with each other and what extreme values can be achieved), b) gather correlation information during the optimization process (how achieved values in objectives correlate with changes in other objectives achieved values), c) create disturbed optimization processes from a local, stable solution, thus achieving information as to what can be done to move in different alternative solutions, or d) by using external artificial intelligence models or libraries that provide more information about similar situations.

After the computer identifies a converged, optimal radiotherapy treatment plan, the computer may present the results (e.g., the projected dosage different organs will receive under the plan) to a physician on a user interface. The physician may view the user interface and query the computer (e.g., using the computer device presenting the results on the user interface) for different information. In one example, the physician may query the computer for the status (e.g., the gathered information) for each objective. The physician may view lists of objectives sorted by importance, relevance, or any given quality aspect. This information may give users a better understanding as to why the radiotherapy treatment plan reached its optimal state.

In another example, the physician may ask for guidance. The physician may ask questions, such as "why isn't this objective met?" Such questions may be picked from a list of pre-set questions. In some cases, the computer may support a language-interpretation model (e.g., a natural language protocol). In such cases, a question may be written in textual form using normal human language, or asked directly using a microphone. The answers to such questions may be likewise produced using either pre-set answer-formatting, or produced vocally (e.g., vocally produced using artificial intelligence techniques) through speakers.

In yet another example, the physician may give commands as to how to continue the optimization from the existing situation. The commands can be chosen from preset templates, such as: "Achieve a value of X in the objective dimension," "Give 5% lower MU's," etc. The commands can be also written or vocally given via microphone if the AI model supports it. Since this process may produce a new optimized plan, the new plan may be saved and/or stored in a separate state such that the physician can return to the previously optimized plan.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of this disclosure or the claims.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the claimed features or this disclosure. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the embodiments described herein and variations thereof. Various modifications to these embodiments will be readily apparent to those skilled in the art, and the principles defined herein may be applied to other embodiments without departing from the spirit or scope of the subject matter disclosed herein. Thus, the present disclosure is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What I claim is:

1. A method comprising:
   monitoring, by a processor, a computer model generating a radiation therapy treatment plan comprising a projected dose-volume distribution for a structure of a patient, the computer model receiving at least an image of the structure of the patient and a dose objective, wherein the computer model iteratively calculates the treatment plan by projecting different doses for the structure of the patient until the computer model converges onto the projected dose-volume distribution;
   generating, by the processor based on the iterative calculations of the treatment plan, a data structure comprising correlation values indicating the amount of radiation individual structures of the patient are projected to receive as a result of adjusting the amount of radiation other structures of the patient are projected to receive;
   receiving, by the processor from a computer device presenting the radiation treatment plan, a query indicating the structure of the patient or an attribute of the radiation therapy treatment plan;
   generating, by the processor, a query term based on the received query;
   retrieving, by the processor, a correlation value associated with the query term by querying the data structure; and
   transmitting, by the processor, data generated based on the correlation value to the computer device, wherein the generated data corresponds to a second structure and at least one projected different dose.

2. The method of claim 1, further comprising:
   instructing, by the processor, the computer device to display the retrieved data in a window associated with the presentation of the radiation therapy treatment plan.

3. The method of claim 2, wherein the display is at least one of a chart, a sentence in a natural language, or a number.

4. The method of claim 1, wherein generating the query term comprises executing, by the processor, a natural language processing protocol to identify the query term.

5. The method of claim 1, wherein retrieving the correlation value associated with the query term comprises retrieving a positive or negative correlation between the structure and the second structure.

6. The method of claim 1, wherein the radiation therapy treatment plan further comprises a monitored unit (MU) parameter, wherein the computer model converges onto the projected dose-volume distribution and the MU parameter.

7. The method of claim 6, wherein the computer model converges onto the projected dose-volume distribution and the MU parameter using a cost function, and further comprising monitoring, by the processor, a parameter of the cost function associated with at least a portion of a projected dose-volume distribution from at least one iteration and a corresponding MU.

8. The method of claim 1, wherein the second structure is the same as the structure.

9. A system comprising:
   a processor configured to:
      monitor a computer model generating a radiation therapy treatment plan comprising a projected dose-volume distribution for a structure of a patient, the computer model receiving at least an image of the structure of the patient and a dose objective, wherein the computer model iteratively calculates the treatment plan by projecting different doses for the structure of the patient until the computer model converges onto the projected dose-volume distribution;
      generate, based on the iterative calculations of the treatment plan, a data structure comprising correlation values indicating the amount of radiation individual structures of the patient are projected to receive as a result of adjusting the amount of radiation other structures of the patient are projected to receive;
      receive, from a computer device presenting the radiation treatment plan, a query indicating the structure of the patient or an attribute of the radiation therapy treatment plan;
      generate a query term based on the received query;
      retrieve a correlation value associated with the query term by querying the data structure data; and
      transmit data generated based on the correlation value to the computer device, wherein the generated data corresponds to a second structure and at least one projected different dose.

10. The system of claim 9, wherein the processor is further configured to:
   instruct the computer device to display the retrieved data in a window associated with the presentation of the radiation therapy treatment plan.

11. The system of claim 10, wherein the display is at least one of a chart, a sentence in a natural language, or a number.

12. The system of claim 9, wherein the processor is configured to generate the query term by executing a natural language processing protocol to identify the query term.

13. The system of claim 9, wherein the processor is configured to retrieve the correlation value associated with the query term by retrieving a positive or negative correlation between the structure and the second structure.

14. The system of claim 9, wherein the radiation therapy treatment plan further comprises a monitored unit (MU) parameter, wherein the computer model converges onto the projected dose-volume distribution and the MU parameter.

15. The system of claim 14, wherein the computer model converges onto the projected dose-volume distribution and the MU parameter using a cost function, and wherein the processor is configured to monitor a parameter of the cost function associated with at least a portion of a projected dose-volume distribution from at least one iteration and a corresponding MU.

16. The system of claim 9, wherein the second structure is the same as the structure.

17. A method comprising:
monitoring, by a processor, a computer model generating a radiation therapy treatment plan comprising a projected dose-volume distribution for a structure of a patient, the computer model receiving at least an image of the structure of the patient and a dose objective, wherein the computer model iteratively calculates the treatment plan by projecting different doses for the structure of the patient until the computer model converges onto the projected dose-volume distribution;

in response to a presentation of the radiation therapy treatment plan by a computer device, receiving, by the processor, a query indicating the structure of the patient or an attribute of the radiation therapy treatment plan and a new objective of the radiation therapy treatment plan; and instructing, by the processor, the computer model to execute a simulation of an additional iteration using the new objective.

18. The method of claim 17, further comprising:
instructing, by the processor, the computer device to display data associated with a new radiation therapy treatment plan using the new objective.

19. The method of claim 18, wherein the new radiation therapy treatment plan includes a cost function parameter associated with the new objective.

20. The method of claim 18, wherein at least a difference between the radiation treatment plan and the new radiation treatment plan is indicated.

* * * * *